US012702492B2

(12) United States Patent
Vigh et al.

(10) Patent No.: US 12,702,492 B2
(45) Date of Patent: Aug. 11, 2026

(54) SYSTEMS AND METHODS FOR AUTOMATIC OBLIQUE LATERAL INTERBODY FUSION (OLIF) CORRIDOR PLANNING

(71) Applicant: Medtronic Navigation, Inc., Lafayette, CO (US)

(72) Inventors: Rowena O. Vigh, Erie, CO (US); Nikhil Mahendra, Broomfield, CO (US); Andrew J. Wald, Fort Worth, TX (US)

(73) Assignee: MEDTRONIC NAVIGATION, INC., Lafayette, CO (US)

( * ) Notice: Subject to any disclaimer, the term of this patent is extended or adjusted under 35 U.S.C. 154(b) by 194 days.

(21) Appl. No.: 18/672,966

(22) Filed: May 23, 2024

(65) Prior Publication Data

US 2024/0341863 A1 Oct. 17, 2024

Related U.S. Application Data

(63) Continuation of application No. 17/370,176, filed on Jul. 8, 2021, now Pat. No. 11,992,274.

(51) Int. Cl.
*A61B 34/20* (2016.01)
*A61B 6/12* (2006.01)
(Continued)

(52) U.S. Cl.
CPC ................ *A61B 34/20* (2016.02); *A61B 6/12* (2013.01); *A61B 34/10* (2016.02); *A61B 34/25* (2016.02); *A61B 2034/107* (2016.02)

(58) Field of Classification Search
CPC .......... A61B 34/20; A61B 34/10; A61B 34/25
See application file for complete search history.

(56) References Cited

U.S. PATENT DOCUMENTS 7,697,972 B2 4/2010 Verard et al.
8,644,907 B2 2/2014 Hartmann et al.
(Continued)

FOREIGN PATENT DOCUMENTS

WO 2021038202 A1 3/2021
WO 2022101896 A1 5/2022

OTHER PUBLICATIONS

Pojskic et al. (Intraoperative Computed Tomography-Based Navigation with Augmented Reality for Lateral Approaches to the Spine, MDPI, Brain Sci., 2021, 11, 646. https://doi.org/ 10.3390/brainsci11050646, Accepted: May 12, 2021, Published: May 15, 2021).*
(Continued)

*Primary Examiner* — Hugh Maupin
(74) *Attorney, Agent, or Firm* — FOX ROTHSCHILD LLP

(57) ABSTRACT

A surgical navigation and planning system is disclosed. The system may include at least one processor, and a storage medium storing programming instructions. The programming instructions may cause the processor to receive patient-specific vertebrae information include at least one image which may be acquired by an X-ray. The system may perform segmentation of objects in the at least one image and automatically select a set of objects for planning an optimal trajectory to a location proximal the vertebrae level. The system may determine boundary dimensions of an interbody implant, a first entry incision location and a first path for the interbody implant from the first entry incision location to the location proximal the vertebrae level. The system may calculate a plurality of clearance distances between the boundary dimensions and the set of objects. The set of objects may include the psoas muscle, Aorta, and/or Vena Cava.

20 Claims, 8 Drawing Sheets

(51) Int. Cl.
*A61B 34/00* (2016.01)
*A61B 34/10* (2016.01)

(56) References Cited

U.S. PATENT DOCUMENTS

| | | | | |
|---|---|---|---|---|
| 8,842,893 | B2 | 9/2014 | Teichman et al. | |
| 10,092,412 | B2 | 10/2018 | Drochner et al. | |
| 10,517,680 | B2 | 12/2019 | Moctezuma et al. | |
| 10,699,414 | B2 | 6/2020 | Veni et al. | |
| 10,736,699 | B2 | 8/2020 | Ronen et al. | |
| 10,896,508 | B2 | 1/2021 | El Harouni et al. | |
| 10,973,648 | B1 * | 4/2021 | Abdou | A61F 2/4611 |
| 10,984,530 | B1 | 4/2021 | Yao et al. | |
| 11,232,319 | B2 * | 1/2022 | Udupa | G06T 7/136 |
| 2004/0199072 | A1 | 10/2004 | Sprouse et al. | |
| 2011/0160585 | A1 * | 6/2011 | Akyuz | A61B 8/4444<br>600/443 |
| 2011/0306873 | A1 * | 12/2011 | Shenai | A61B 8/0841<br>600/424 |
| 2017/0245947 | A1 | 8/2017 | Bozung et al. | |
| 2018/0092699 | A1 | 4/2018 | Finley | |
| 2020/0121404 | A1 | 4/2020 | Morard et al. | |
| 2020/0146731 | A1 * | 5/2020 | Tillett | A61B 34/30 |
| 2020/0193594 | A1 | 6/2020 | Georgescu et al. | |
| 2020/0261051 | A1 | 8/2020 | Yardibi et al. | |
| 2020/0297424 | A1 | 9/2020 | Helm et al. | |
| 2020/0297425 | A1 | 9/2020 | Helm et al. | |
| 2020/0380696 | A1 | 12/2020 | Feng et al. | |
| 2021/0153955 | A1 | 5/2021 | Krimsky | |
| 2021/0279868 | A1 * | 9/2021 | Ma | A61B 6/032 |
| 2021/0378752 | A1 | 12/2021 | Paul et al. | |
| 2021/0386480 | A1 * | 12/2021 | Tolkowsky | A61B 46/20 |
| 2022/0110701 | A1 | 4/2022 | Crawford et al. | |
| 2022/0138952 | A1 | 5/2022 | Crawford et al. | |
| 2022/0142709 | A1 * | 5/2022 | Zucker | A61B 34/10 |
| 2022/0183755 | A1 | 6/2022 | Finley et al. | |
| 2022/0401062 | A1 * | 12/2022 | Naidu | A61B 8/085 |

OTHER PUBLICATIONS

Chen Liu et al. (A patient with left-sided inferior vena cava who received oblique lumbar interbody fusion surgery: a case report, Liu et al. Journal of Medical Case Reports (2020) 14:21, https://doi.org/10.1186/s13256-020-2342-y, Journal of Medical Case Reports.*

* cited by examiner

SYSTEMS AND METHODS FOR AUTOMATIC OBLIQUE LATERAL INTERBODY FUSION (OLIF) CORRIDOR PLANNING

CROSS REFERENCE TO RELATED APPLICATIONS

This application is a continuation of U.S. patent application Ser. No. 17/370,176, filed Jul. 8, 2021, which incorporates the disclosure of U.S. Pat. No. 7,697,972, entitled, "Navigation System for Cardiac Therapies", filed Jul. 14, 2003; U.S. Pat. No. 8,644,907, entitled, "Method and Apparatus for Surgical Navigation", filed Apr. 29, 2010; U.S. Pat. No. 8,842,893, entitled, "Method and Apparatus for Image-Based Navigation", filed Apr. 30, 2010; and U.S. Pat. App. Pub. No. 2004/0199072, entitled Integration Electromagnetic Navigation and Patient Positioning Device", filed Apr. 1, 2003, in their respective entireties.

FIELD

The present technology is generally related to systems and methods for automatic oblique lateral interbody fusion (OLIF) corridor planning. However, the related systems and methods are not necessarily limited to OLIF corridor planning, and can of course be applied to other parts of the human body.

BACKGROUND

Spinal disorders such as degenerative disc disease, disc herniation, osteoporosis, spondylolisthesis, stenosis, scoliosis, kyphosis and other curvature abnormalities, tumor, and fracture may result from factors including trauma, disease and degenerative conditions caused by injury and aging. Spinal disorders or deformities typically result in symptoms including pain, nerve damage, and partial or complete loss of mobility, at a minimum. Spinal surgery may involve implantation of one or more spinal implants to prevent further deterioration at a vertebra level. This disclosure describes an improvement over these prior art technologies.

SUMMARY

The techniques of this disclosure generally relate to systems and methods for determining an optimal trajectory and/or corridor for performing a surgery utilizing an interbody implant. In some embodiments, the surgery performed may be an Oblique Lateral Interbody Fusion (OLIF) surgery.

In one aspect, the present disclosure provides for a surgical navigation and planning system, for example. In various embodiments, the system may include at least one processor and a non-transitory and tangible computer readable storage medium having programming instructions stored thereon. In various embodiments, the programming instructions may cause the processor to receive patient-specific vertebrae information associated with a vertebrae level for treatment, for example. In various embodiments, the patient-specific vertebrae information may include at least one image. In various embodiments, the system may perform segmentation of objects in the at least one image and automatically select a set of objects for planning a trajectory to a location proximal the vertebrae level, for example. In various embodiments, the system may determine boundary dimensions of an interbody implant, for example. In various embodiments, the interbody implant may be used for insertion along the trajectory, for example. In various embodiments, the system may determine a first entry incision location, for example. In various embodiments, the system may determine a first path for the interbody implant from the first entry incision location to the location proximal the vertebrae level, for example. In various embodiments, the system may calculate, on the basis of the first path, a first plurality of clearance distances between the boundary dimensions of the interbody implant and the set of objects, for example.

In another aspect, the present disclosure provides for a method for determining an optimal oblique corridor for inserting an interbody implant. The method may include the step of providing a surgical navigation and planning system, for example. In various embodiments, the surgical navigation and planning system may include a display and an imaging system including a source for generating X-rays and a detector for detecting X-rays that pass through a patient, for example. In various embodiments, the system may include at least one processor; and a non-transitory and tangible computer readable storage medium having programming instructions stored thereon, for example. The method may further include the step of receiving patient-specific vertebrae information associated with a vertebrae level for treatment, and the patient-specific vertebrae information may include at least one image acquired from the imaging system, for example. The method may further include the steps of performing segmentation of objects in the at least one image and selecting, automatically, a set of objects for planning a trajectory to a location proximal the vertebrae level, for example. In various embodiments, the system may determine boundary dimensions of an interbody implant for inserting along the trajectory, for example. The method may further include the steps of determining a first entry incision location and determining a first path for the interbody implant from the first entry incision location to the location proximal the vertebrae level, for example. The method may further include the step of calculating, on the basis of the first path, a first plurality of clearance distances between the boundary dimensions of the interbody implant and the set of objects, for example. The method may further include the step of displaying, by the display, a viable surgical plan provided the first entry incision location and the first path to navigate around delicate patient tissue within the pre-determined margin of error, for example.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
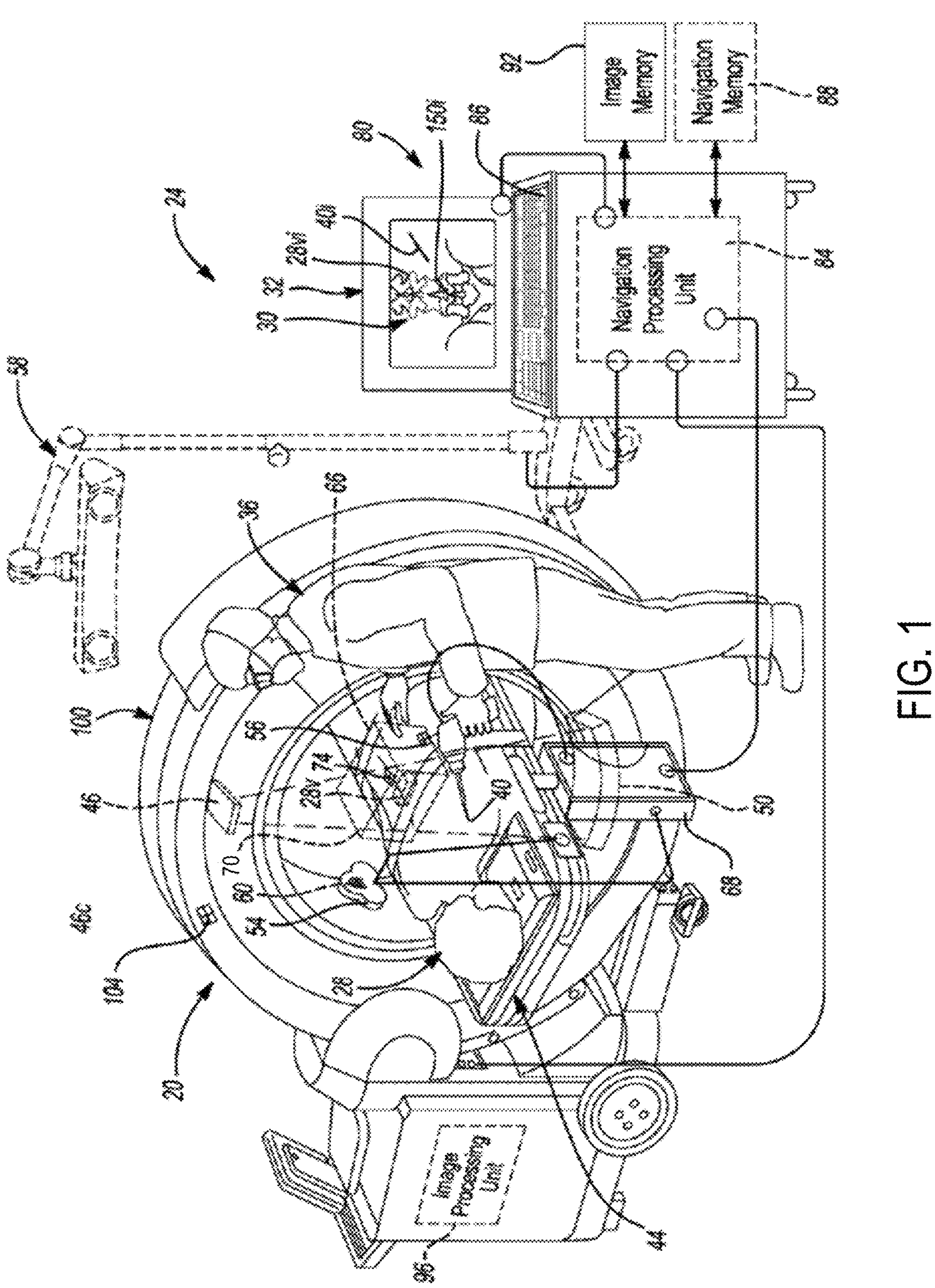
FIG. 1 is an environmental view that illustrates an example navigation system.

The embodiments described herein relate to automatic oblique lateral interbody fusion (OLIF) corridor planning, for example, for implanting an interbody implant for use in treating the deformity, such as by designing a trajectory that accounts for measured distances between the psoas and neighboring vessels.

The planning system of the present disclosure may be understood more readily by reference to the following detailed description of the embodiments taken in connection with the accompanying drawing figures that form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms “a,” “an,” and “the” include the plural, and reference to a particular numerical value includes at least that particular value, unless the context clearly dictates otherwise. Ranges may be expressed herein as from “about” or “approximately” one particular value and/or to “about” or “approximately” another particular value. When such a range is expressed, another embodiment includes from the one particular value and/or to the other particular value. Similarly, when values are expressed as approximations, by use of the antecedent “about,” it will be understood that the particular value forms another embodiment. It is also understood that all spatial references, such as, for example, horizontal, vertical, top, upper, lower, bottom, front, back, left and right, are for illustrative purposes only and can be varied within the scope of the disclosure. For example, the references “upper” and “lower” are relative and used only in the context to the other, and are not necessarily “superior” and “inferior”.

Further, as used in the specification and including the appended claims, “treating” or “treatment” of a disease or condition may refer to planning for and performing a procedure that may include administering one or more drugs to a patient (human or other mammal), employing implantable devices, and/or employing instruments that treat the disease, such as, for example, instruments used to implant bone constructs, interbody implants and screws, for example.

Alleviation can occur prior to signs or symptoms of the disease or condition appearing, as well as after their appearance. Thus, treating or treatment includes preventing or prevention of and/or reducing the likelihood of a certain disease or undesirable condition (e.g., preventing or reducing the likelihood of the disease from occurring in a patient who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term “tissue” includes soft tissue, ligaments, tendons, cartilage and/or bone unless specifically referred to otherwise.

The following disclosure includes a description of a computing system for designing a trajectory through the anatomy of a patient that accounts for measured distances between the psoas and neighboring vessels relative to an interbody implant for passage of the interbody implant proximal to a vertebrae level. The following disclosure includes a description of computer-implemented methods of employing the computing system in accordance with the principles of the present disclosure. Alternate embodiments are also disclosed. Reference is made in detail to the exemplary embodiments of the present disclosure, which are illustrated in the accompanying figures.

The designed implant may be fabricated from biologically acceptable materials suitable for medical applications, including computer aided metals, computer aided plastics, metals, synthetic polymers, ceramics and bone material and/or their composites. For example, the implant may be fabricated from materials such as stainless steel alloys, aluminum, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologic, Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

The implants may have material composites, including the above materials, to achieve various desired characteristics such as strength, rigidity, elasticity, compliance, biomechanical performance, durability and radiolucency or imaging preference. The implants may also be fabricated from a heterogeneous material such as a combination of two or more of the above-described materials.

Example embodiments will now be described more fully with reference to the accompanying drawings. The disclosure incorporates herein by reference in its entirety “OLIF25 Procedure Oblique Lateral Interbody Fusion for L2-L5 Surgical Technique,” by Medtronic Sofamor Danek USA, Inc., copyright 2017.

With reference to FIG. 1, an environmental view of an operating room with an imaging system 20 that may be used with a surgical navigation system 24 is illustrated. The imaging system 20 may be used to image a subject 28. The imaging system 20 may acquire images of the subject 28 at selected times during a procedure. In various embodiments, the imaging system 20 may acquire image data to display and/or generate an image 30 of the subject 28 for display with the display device 32.

The navigation system 24 may be used for various purposes or procedures by one or more users, such as a user 36. The navigation system 24 may be used to determine or track a position of an instrument 40 (e.g. powered tool, implant, etc.) in a volume. The position may include both a three dimensional X,Y,Z location and orientation (angle of attack and/or inclination). Orientation may include one or more degrees of freedom, such as three degrees of freedom. It is understood, however, that any appropriate degree of freedom position information, such as less than six-degree of freedom position information, may be determined and/or presented to the user 36.

Tracking the position of the instrument 40 may assist the user 36 in determining a position of the instrument 40, even if the instrument 40 is not directly viewable by the user 36. Various procedures may block the view of the user 36, such as performing a repair or assembling an inanimate system, such as a robotic system, assembling portions of an airframe or an automobile, etc. Various other procedures may include a surgical procedure, such as performing a spinal procedure, neurological procedure, positioning a deep brain simulation probe, or other surgical procedures on a living subject. For example, a procedure to determine an OLIF corridor. In various embodiments, for example, the living subject may be a human subject 28 and the procedure may be performed on the human subject 28. It is understood, however, that the instrument 40 may be tracked and/or navigated relative to any subject for any appropriate procedure including animals, for example. Tracking or navigating an instrument for a procedure, such as a surgical procedure, on a human or living subject is merely an example.

In various embodiments, the surgical navigation system 24, as discussed further herein, may incorporate various portions or systems, such as those disclosed in U.S. Pat. Nos. 7,697,972; 8.644.907; and 8,842,893; and U.S. Pat. App. Pub. No. 2004/0199072, all incorporated herein by reference. Various components or systems may be used in combination with or incorporated with the navigation system 24, such as the imaging system 20. It is understood, however, that the imaging system 20 may be used separate and independent of the navigation system 24.

The imaging system 20 operable to image the subject 28 can include, an O-Arm® imaging system, magnetic resonance imaging (MRI) system, fluoroscopy, computed tomography (CT) system, etc. A subject support 44 may be used to support or hold the subject 28 during imaging and/or during a procedure. The same or different supports may be used for different portions of a procedure.

In various embodiments, the imaging system 20 may include a source 46. The source 46 may emit and/or generate X-rays. The X-rays may form a cone **46*c*, such as in a cone beam, that impinge on the subject 28. Some of the X-rays pass though and some are attenuated by the subject 28. The imaging system 20 may further include a detector 50 to detect the X-rays that are not completely attenuated, or blocked, by the subject 28**. Thus, the image data may include X-ray image data. Further, the image data may be two-dimensional (2D) image data and/or three-dimensional (3D) image data, for example.

Image data may be acquired, such as with one or more of the imaging systems 20 discussed above, during a surgical procedure, prior to a surgical procedure, or subsequent to a procedure for displaying the image 30 on the display device 32, for example. In various embodiments, the acquired image data may also be used to form or reconstruct selected types of image data, such as three-dimensional volumes, even if the image data is 2D image data. In various embodiments, as discussed herein, the image data may include various portions (e.g. the instrument 40) that is within the image 30. Selected processor systems, as discussed herein, may be used to segment the instrument 40 from other portions within the image 30, as also discussed herein.

The instrument 40 may be tracked in a trackable volume or a navigational volume by one or more tracking systems. Tracking systems may include one or more tracking systems that operate in an identical manner or more and/or different manner or mode. For example, the tracking system may include an electro-magnetic (EM) localizer 54, as illustrated in FIG. 1. In various embodiments, it is understood by one skilled in the art, that other appropriate tracking systems may be used, e.g., including optical (including an optical or camera localizer 58), radar, ultrasonic, etc. The discussion herein of the EM localizer 54 and tracking system is merely an example of various tracking systems operable with the navigation system 24. The position of the instrument 40 may be tracked in the tracking volume relative to the subject 28 and then illustrated as a graphical representation or graphical overlay, also referred to as an icon **40*i* with the display device 32. In various embodiments, the icon 40*i* may be superimposed on the image 30 and/or adjacent to the image 30. As discussed herein, the navigation system 24 may incorporate the display device 30 and operate to render the image 30 from selected image data, display the image 30, determine the position of the instrument, determine the position of the icon 40*i***, etc.

With reference to FIG. 1, the EM localizer 54 is operable to generate electro-magnetic fields with an included transmitting coil array (TCA) that includes one or more transmitting conductive coils 60 which is incorporated into the localizer 54. The localizer 54 may include one or more coil groupings or arrays. In various embodiments, more than one group is included and each of the groupings may include three coils, also referred to as trios or triplets. The coils may be powered to generate or form an electro-magnetic field by driving current through the coils of the coil groupings. As the current is driven through the coils, the electro-magnetic fields generated may extend away from the localizer 54 and form a navigation domain or volume 66, such as encompassing all or a portion of a head, spinal vertebrae **28*v*, or other appropriate portion. The coils may be powered through a TCA controller and/or power supply 68. It is understood, however, that more than one of the EM localizers 54** may be provided and each may be placed at different and selected locations.

The navigation domain or volume 66 generally defines a navigation space or patient space. The instrument 40, such as a drill, lead, implant (e.g. screw) etc., may be tracked in the navigation space that is defined by a navigation domain relative to a patient or subject 28 with an instrument tracking device. For example, the instrument 40 may be freely moveable, such as by the user 36, relative to a dynamic reference frame (DRF) or patient reference frame tracker 74 that is fixed relative to the subject 28. Tracking devices 70, 74 may include tracking portions that are tracking with appropriate tracking systems, such as sensing coils (e.g. conductive material formed or placed in a coil) that senses and are used to measure a magnetic field strength, optical reflectors, ultrasonic emitters, etc. Due to the instrument tracking device 70 connected or associated with the instrument, relative to the DRF 74, the navigation system 24 may be used to track the position of the instrument 40 relative to the DRF 74.

The navigation volume or patient space may be registered to an image space defined by the image 30 of the subject 28 and the icon 40 *i* representing the instrument 40 may be illustrated at a navigated (e.g. determined) and tracked position with the display device 32, such as superimposed on the image 30. Registration of the patient space to the image space and determining a position of a tracking device, such as with the tracking device 70, relative to a DRF, such as the DRF 74, may be performed as generally known in the art, including as disclosed in U.S. Pat. Nos. 7,697,972; 8.644.907; and 8,842,893; and U.S. Pat. App. Pub. No. 2004/0199072, all incorporated herein by reference.

The navigation system 24 may further include a navigation processor system 80. The navigation processor system 80 may include the display device 32, the localizer 54, the TCA controller 68, and other portions and/or connections thereto. For example, a wire connection may be provided between the TCA controller 68 and a navigation processing unit 84. Further, the navigation processor system 80 may have one or more user control inputs, such as a keyboard 86, and/or have additional inputs such as from communication with one or more navigation memory systems 88, either integrated or via a communication system. Additional and/or alternative memory systems 92 may also be accessed including analysis memory that may include image memory, model (e.g. computer aided drafting (CAD) models having dimensions and materials, known component (e.g. x-ray attenuation relative to material information)), etc. The navigation processor system 80 may, according to various embodiments include those disclosed in U.S. Pat. Nos. 7,697,972; 8,644,907; and 8,842,893; and U.S. Pat. App. Pub. No. 2004/0199072, all incorporated herein by reference, or may also include the commercially available StealthStation® or Fusion™ surgical navigation systems sold by Medtronic Navigation. Inc. having a place of business in Louisville. Colorado.

Tracking information, including information regarding the electro-magnetic fields sensed with the tracking devices 70, 74 may be delivered via a communication system, such as the TCA controller 68, which also may be a tracking device controller, to the navigation processor system 80 including the navigation processor 84. Thus, the tracked position of the instrument 40 may be illustrated as the icon 40*i* relative to the image 30. Various other memory and processing systems may also be provided with and/or in communication with the processor system 80, including the memory system 88 that is in communication with the navigation processor 84 and/or an imaging processing unit 96. Such memory may be physical memory in the form of a data store and/or non-transitory computer readable medium such as RAM and/or DRAM and/or cloud based memory storage solutions, for example.

The image processing unit 96 may be incorporated into the imaging system 20, such as the O-Arm® imaging system, as discussed above. The imaging system 20 may include various additional portions such as a gantry 100 within which the source 46 and the x-ray detector 50 are moveable. The imaging system 20 may also be tracked with a tracking device 104. It is understood, however, that the imaging system 20 need not be present while tracking the tracking devices, including the instrument tracking device 40. Further, the imaging system 20 need not be present in an operation or procedure room. The illustration including the imaging system 20 is merely for explanation and/or example disclosure with reference to the present disclosure and it is understood that the imaging system 20 and/or the subject 28 may be moved for a selected image acquisition procedure before, after, or during a selected procedure. Also, the imaging system 20 may be any appropriate imaging system including a MRI, CT, etc., for example.

The image 30 that is displayed with the display device 32 may be based upon image data that is acquired of the subject 28 in various manners. For example, the imaging system 24 may be used to acquire image data that is used to generate the image 30. It is understood, however, that other appropriate imaging systems may be used to generate the image 30 using image data acquired with the selected imaging system. Imaging systems may include magnetic resonance imagers, computed tomography imagers, and other appropriate imaging systems. Further the image data acquired may be two dimensional or three dimensional data and may have a time varying component, such as imaging the patient during a heart rhythm and/or breathing cycle.

In various embodiments, the image data is a 2D image data that is generated with a cone beam. The cone beam that is used to generate the 2D image data may be part of an imaging system, such as the O-Arm® imaging system. The 2D image data may then be used to reconstruct a 3D image or model of the imaged subject, such as the subject 28. The reconstructed 3D image and/or an image based on the 2D image data may be displayed. Thus, it is understood by one skilled in the art that the image 30 may be generated using the selected image data, such as from the imaging system 20.

The image 30 is generated from image data of the subject 28 that is acquired with the imaging system 20. In various embodiments, the image data that is used to generate the image 30 may include image data of the screw 150. The screw 150, for example, may be implanted in the subject 28. As is understood by one skilled in the art, an image of the subject 28 may be acquired or generated after placing the screw 150, or more than one screw 150, in the subject 28. The image data acquired of the subject after placing the screw 150 may be to confirm and/or evaluate the position of the screw 150 in the subject 28. The screw 150 may be used to secure an interbody implant, for example. In various embodiments, it is understood by one skilled in the art, that the image data and/or resulting or generated image 30 may be used to confirm the placement of any appropriate member or implant including a screw, interbody implant, cage, etc. Thus, the screw 150 is merely exemplary.

Accordingly, the image 30 may include a first vertebrae 28*vi* image of a vertebrae 28*v*. Further, the image 30 may include an implant or screw image 150*i* (which may be the instrument 40, as discussed above). The screw image 150*i* may be further delineated or segmented, as discussed herein.

According to various embodiments, the image 30 may be segmented in a substantially automatic manner. In various embodiments, the automatic segmentation may be incorporated into a neural network. The neural network may be designed to learn or determine selected weights for activating different neurons in the network for identifying features, and applications such as segmenting an item in an image. Neural networks may include various types of networks, such as a convolutional neural network (CNN). The CNN may be taught or determine or may learn to determine, such as with a probability or prediction, various features in the image 30 (and/or the image data used to generate the image 30), according to various embodiments. Various features may include objects such as the screw 150 and/or portions thereof, such as with segmentations or boundaries of these objects or portions. The selected segmentations may include identifying a segmentation of the screw 150 in the image and may further include segmenting separate portions of the screw 150, for example.

Figure 2:
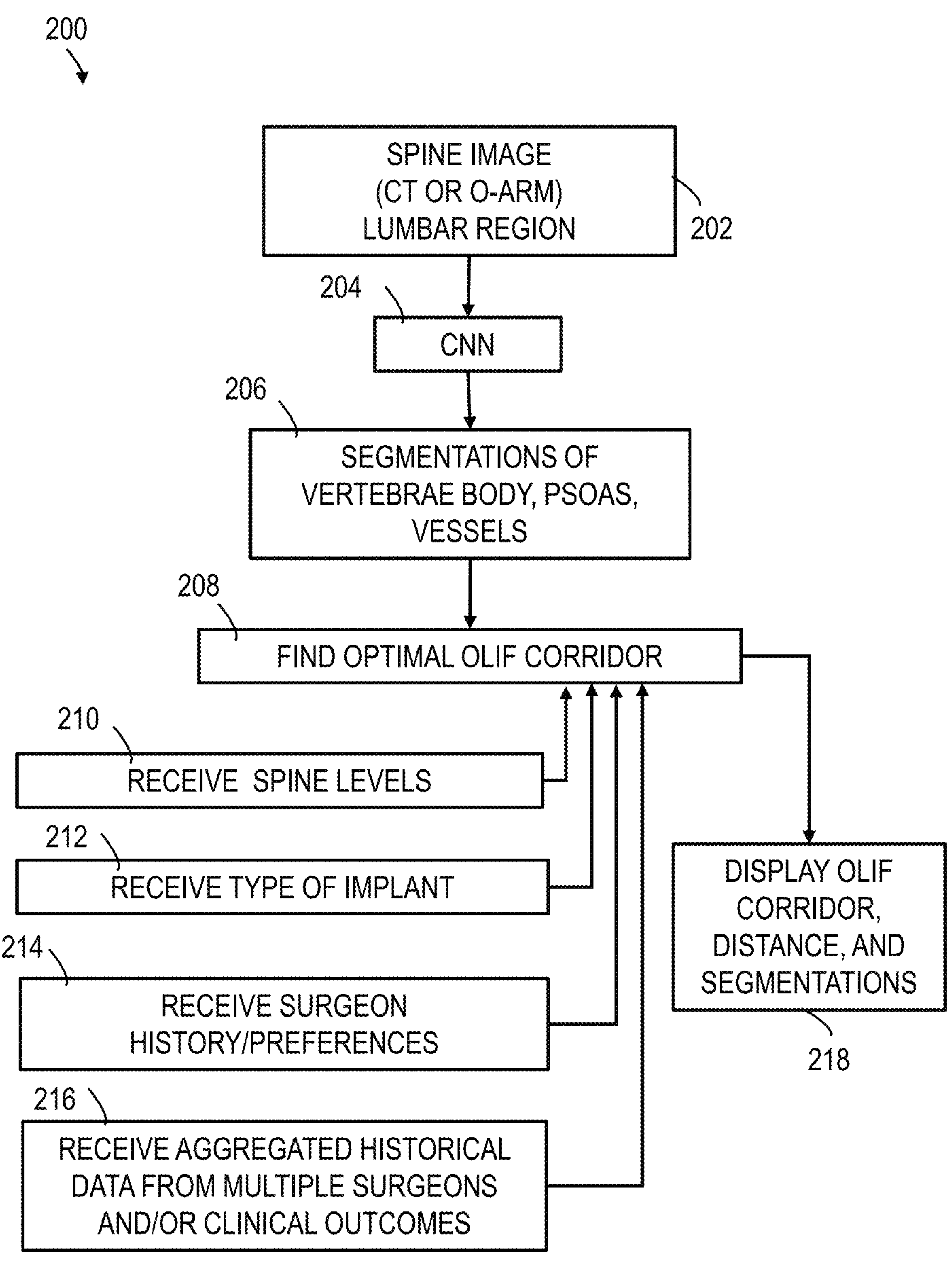
FIG. 2 is a flowchart that illustrates a method for automatic OLIF corridor planning.

FIG. 2 is a flow diagram that illustrates a method 200 for automatic OLIF corridor planning. The method steps may be performed in the order shown or a different order. One or more of the steps may be performed contemporaneously. One or more steps may be added or deleted in an instantiation. The method 200 may be described in relation to FIGS. 4A-4B, 5, and 6, for example. The method 200 may also be described in relation to FIG. 7.

The method 200 may include (at step 202) receiving an image 400*a* (see FIG. 4A), for example, of the subject area, such as the spine of a patient. The image 400A may be captured by an O-Arm® imaging system, magnetic resonance imaging (MRI) system, fluoroscopy, computed tomography (CT) system, etc. In some embodiments, the received image 400A may be a selected image stored in a remote server 790 (FIG. 7) where two-dimensional images 795 (FIG. 7) of the patient are stored. Alternately or in addition to, images may be captured by the imaging system 20 (FIG. 1).

Figure 7:
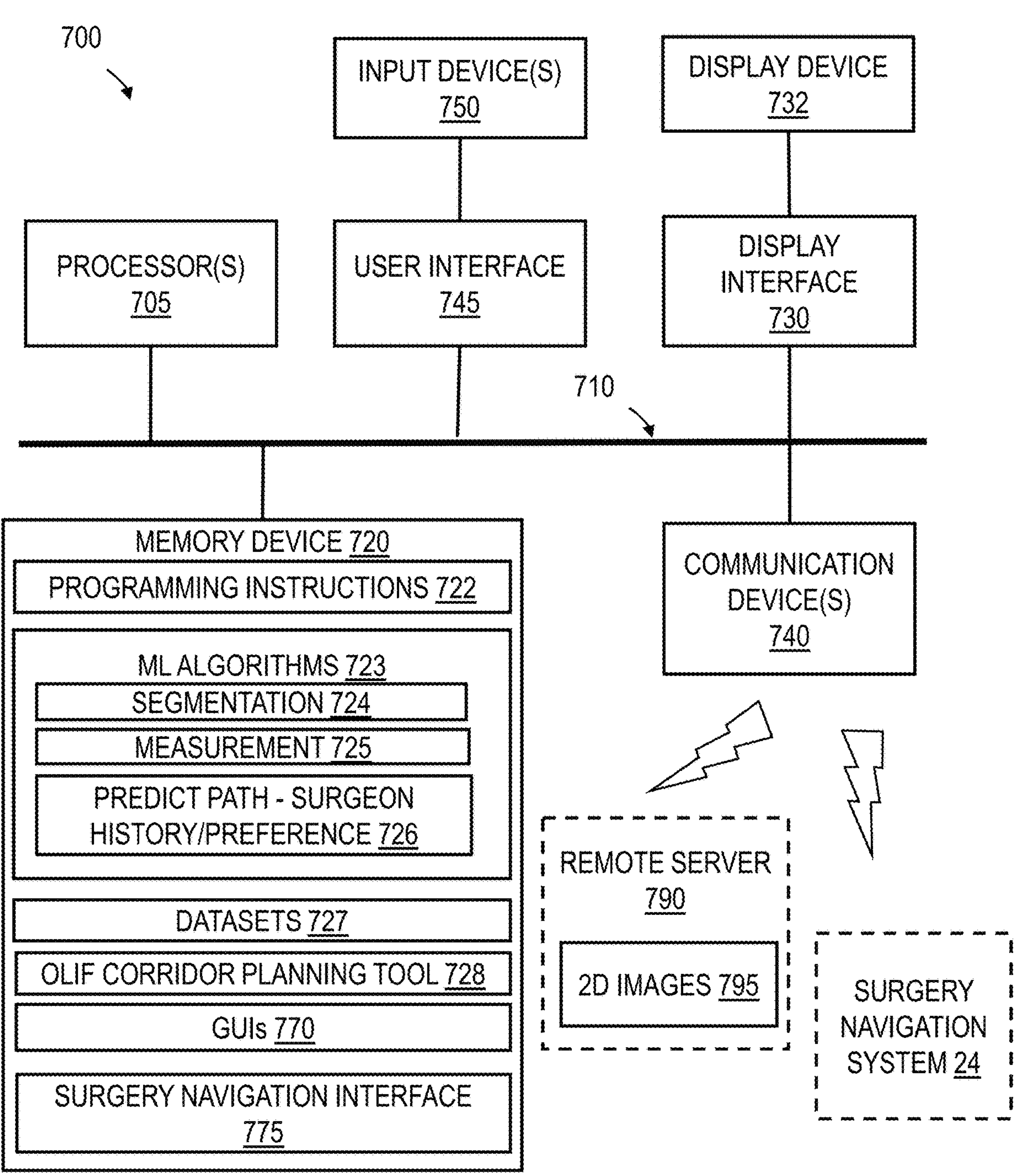
FIG. 7 illustrates an example systems diagram of internal hardware that may be included in any of the electronic components of an external electronic device in accordance with the principles of this disclosure.

The method may include (at step 204), by at least one processor 705 (see FIG. 7), performing at least one machine-learning algorithm 723 (see FIG. 7). The machine-learning algorithm(s) 723 may include one or more of a Generative Adversarial Network (GAN) algorithm, a Convolutional Neural Network (CNN) algorithm, an Autoencoder algorithm, and/or a Recurrent Neural Network (RNN) algorithm, linear regression, Support Vector Machine (SVM) algorithm, Support Vector Machine-Regression (SVR) algorithm, and/or any combination thereof. For example, in some embodiments, the at least one processor 705 may be configured to utilize a combination of a CNN algorithm with an SVM algorithm.

Figure 4A:
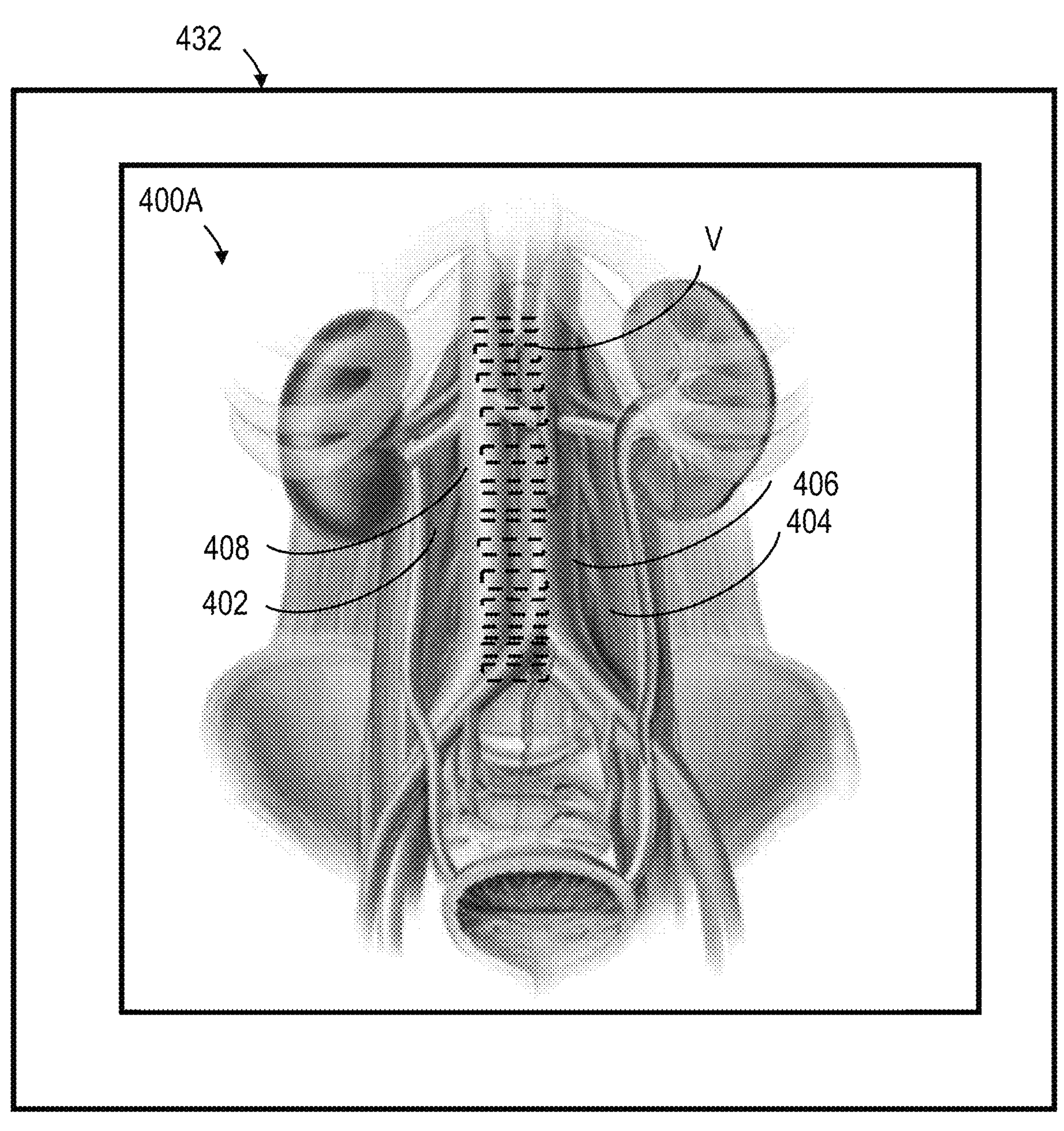
FIG. 4A is an image that illustrates a psoas, vessels and vertebra bodies shown in phantom lines.
Figure 4B:
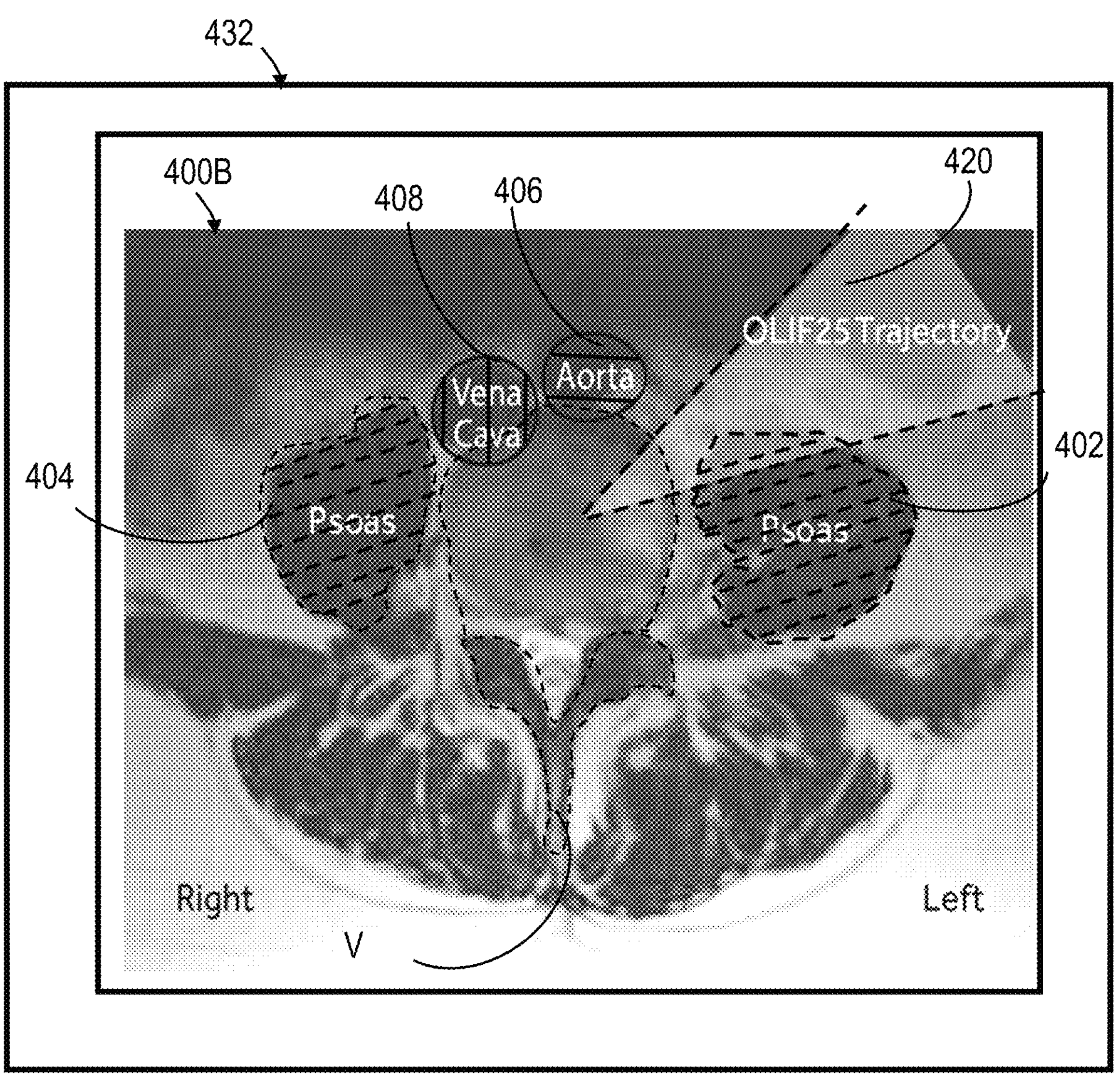
FIG. 4B is an image that illustrates segmented psoas and vessels having overlaid masks.

With reference to FIG. 4A, an image for use with the disclosed method of FIG. 2 will be disclosed. For example, FIG. 4A is an image 400A that illustrates a psoas 402, 404, vessels 406, 408 and vertebra bodies V shown in phantom. FIG. 4B is an image 400B that illustrates segmented psoas 402, 404 and vessels 406, 408. In FIG. 4B, the image 400B illustrates object segmentation that may include identifying and labeling psoas 402, 404, Aorta 406 and Vena Cava 408. The illustrated masks are for illustrative purposes only and are represented as hatched lines. For example, the dashed hatched lines represent a mask for the psoas 402 and horizontal hatched lines for the Aorta 406. The Vena Cava 408 is shown with vertical hatched lines.

The method 200 may include (at step 206), by at least one processor 705, performing segmentation of the vertebrae body V, psoas 402, 404 (see FIGS. 4A and 4B) and/or vessels 406, 408 in the image 400B, for example, as shown in FIG. 4B. The vessels may be an Aorta and Vena Cava, for example. Segmentation of the image 400B may be used to determine and/or delineate anatomical muscles, discs, vessels, and/or vertebrae bones in the image 400B, for example. Image 400B may be, for example, a particular vertebrae level of image 400A that may be treated with an implant, and/or spinal construct, for example.

Various masks may be represented on the display 432, for example. The representation may be shown on the display 432 such as with a graphical representation or a graphical overlay of the mask, for example. The segmentation of the image 400B may identify objects within the image, for example. In some embodiments, objects within the image may include the psoas muscle, nerve endings, the aorta, the vena cava, and/or other at-risk patient tissue. In some embodiments, objects within the image may include prior installed biomechanical hardware, such as plates, pins, rods, interbody implants, etc. This image 400B may be used for surgery planning. Additionally, the image 400B may also be used as a label for segmenting those various images that may be captured during surgery.

With reference back to FIG. 2, the method 200 may include (at step 208), by at least one processor 705, finding an OLIF corridor 420 proximal to and/or granting access to a subject vertebrae body V. The OLIF corridor 420 may be an optimal trajectory to the vertebra body V, through which an interbody implant 551 may pass, for example. The trajectory may be configured to avoid the psoas and provide a trajectory that will maximize the distance between the surgical instrument and nerves. In some embodiments, such distance may not necessarily be maximized but will instead be sufficient to avoid such delicate patient tissue within a known margin of error (and/or a predetermined margin of error), for example. In various embodiments, the motor nerves may be on the posterior side or end of the psoas, for example (depending on orientation of course). The trajectory to the entry point into the vertebrae body V may be planned to minimize the distance to the Aorta and Vena Cava, for example. In some embodiments, such distance may not necessarily be maximized but will instead be sufficient to avoid such delicate patient tissue within a known margin of error, for example. The trajectory may be planned along a nerve-free pathway. More importantly, the trajectory may approach the entry point from a more anterior angle than the midpoint of the vertebral body, for example.

The machine-learning algorithms 723 may employ supervised machine learning, semi-supervised machine learning, unsupervised machine learning, deep learning and/or reinforcement machine learning, for example. The method 200 may include (at step 210), by the at least one processor 705, receiving information (and/or storing information) associated with at least one level of the spine to be treated, for example. The method 200 may include (at step 212), by at least one processor 705, receiving information (and/or storing information) associated with at least one implant for planning the surgery, for example. The at least one implant may include an interbody implant. An example interbody implant is described in U.S. Pat. No. 10,092,412, entitled "INTERBODY IMPLANT SYSTEM AND SYSTEM," incorporated herein by reference in its entirety.

The method 200 may include (at step 214), by the at least one processor 705, receiving information associated with a surgeon's history and/or individual preference(s), for example. In various embodiments, this may include information associated with the surgeon's prior path direction and incision location, for the same and/or similar vertebra level. For example, historical information pertaining to the surgeon's prior path direction and incision location. Similarly, one surgeon may load the particular preferences of an alternate surgeon who may be more experienced and/or have conducted more surgeries of a particular kind or type, for example. The method 200 may include (at step 216), by the at least one processor 705, receiving information associated with aggregated historical data from multiple surgeons and/or clinical outcomes, for example. The received information may be processed (at step 208) and displayed (at step 218)

of the OLIF corridor including a distance and segmentations, for example, that may be displayed on the display device 432 such that an end use may view the displays. For example, as shown in FIG. 4B. The information received at steps 210, 212, 214 and 216 may be stored in the datasets 727 (FIG. 7) and/or local physical memory or external cloud based memory on a network, for example.

Figure 3:
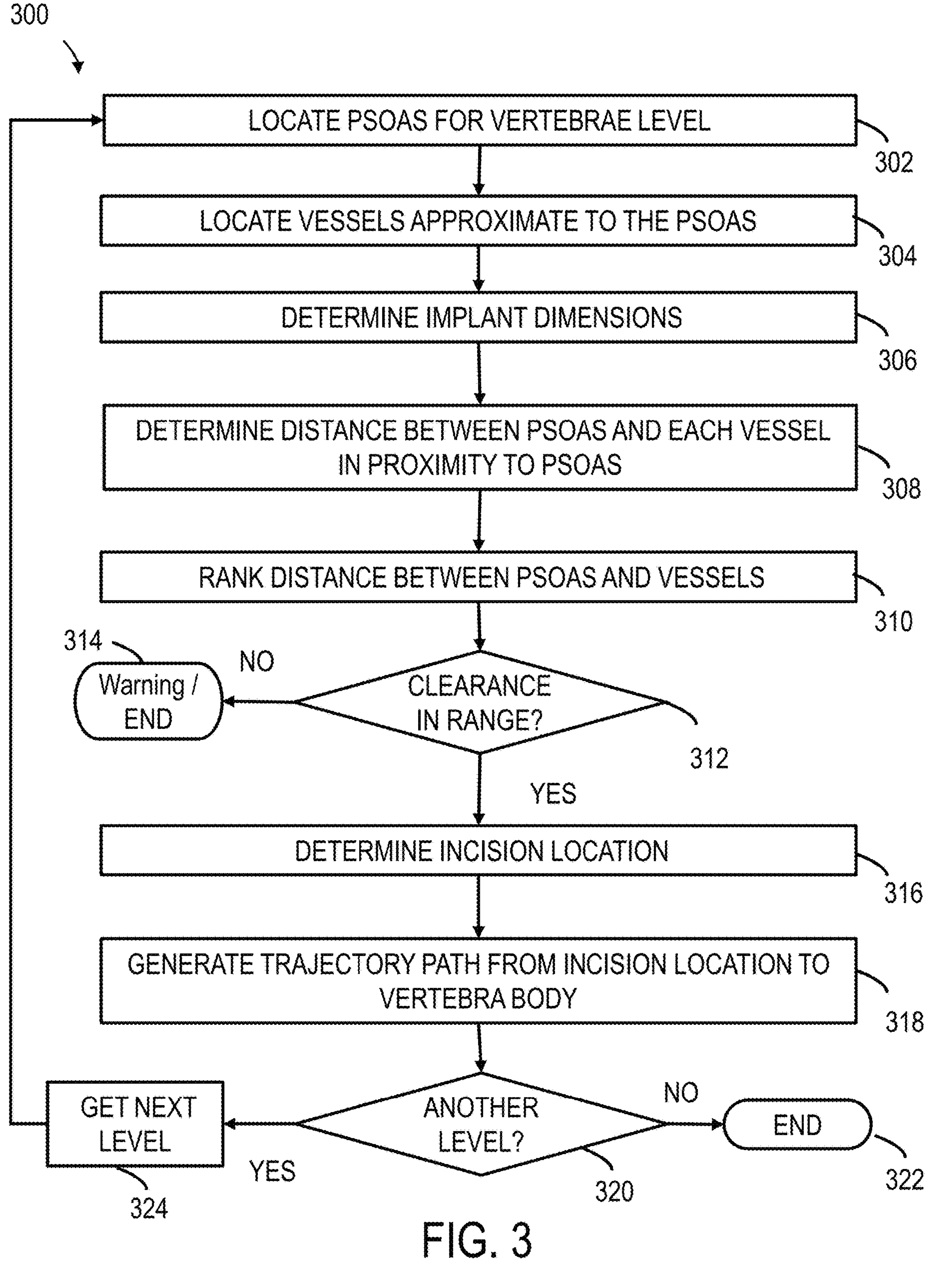
FIG. 3 is a flowchart that illustrates a method for finding a patient-specific OLIF trajectory.

FIG. 3 is a flowchart that illustrates a method 300 for finding a patient-specific OLIF trajectory. In some embodiments, method 300 may comprise a sub-routine broadly relevant to and/or performed at step 208 (see FIG. 2). The method 300 may include (at step 302), by at least one processor 705, locating a psoas 402 or 404 adjacent to a vertebrae level that may be selected for treatment, for example. The method 300 may include (at step 304), by at least one processor 705, locating vessels (e.g., Aorta 406 and Vena Cava 408) proximate and/or adjacent to the psoas 402 or 404 in proximity to a respective vertebrae level selected for treatment. The method 300 may include (at step 306), by at least one processor 705, determining three-dimensional (3D) dimensions of an interbody implant 551 to be implanted proximal the vertebrae level. The at least one processor 705, when determining the implant's dimensions may also estimate six degrees of freedom associated with possible estimated poses of the implant.

The method 300 may include (at step 308), by at least one processor 705, determining a distance between the psoas 402 or 404 and each vessel (e.g., Aorta 406 and/or Vena Cava 408) in proximity to the psoas 402 or 404, for example. The method 300 may include (at step 310), by at least one processor 705, ranking the distances between the psoas and the Aorta and/or distances between the psoas and the Vena Cava, for example. For example, a multitude of surgical paths may be analyzed and the system may rank the paths according to distances between the psoas and the Aorta, for example. The method 208 may include (at step 312), by at least one processor 705, determining whether the distances meet a clearance range and/or have an appropriate factor of safety. In some embodiments, the clearance range may be a predetermined range stored on the system and in other embodiments the clearance range may be programmed on the fly at the time of the particular surgery. In various embodiments, the clearance range may be determined based on the size of the implant and/or surgical instrumentation, for example. In various embodiments, the system itself may update the clearance range and/or appropriate factory of safety based on prior surgeries. For an example, a prior surgery may have been performed with a substantially similar implant having substantially similar boundary conditions and the surgical path and outcome may be used to calculate an appropriate clearance range. If the determination (at step 312) is "NO," the method 300 may end (at step 314 for example). In various embodiments, a display alert may be displayed by the display device 432 if the trajectory cannot be found. If the determination (at step 312) is "YES," the method 300 may include (at step 316) determining an incision location for the vertebrae level, for example. Additionally, in various embodiments, at STEP 314—the system may continuously and automatically monitor the installation of an implant along the optimal trajectory in real time and display a warning if needed. For example, in an instance such as when there is a deviation from the optimal trajectory during the installation thereof by either the implant, instrument, instrument tip, and/or surgical tool the system may display a warning. The warning may include such relevant information as the extent of the deviation and provide a direction and/or suggestion for correction of the actual trajectory back towards the optimal trajectory. Additionally, in some embodiments these "warnings" may be in tiers with a yellow warning (slight deviation), orange warning (medium deviation), and red warning (significant deviation). In various embodiments, a yellow warning may still be within the clearance range of avoiding at risk structures as explained previously but still slightly off the optimal trajectory. An orange warning may be nearing the clearance range but still able to avoid at risk structures. A red warning may be such a significant deviation that if further advancement of the implant, instrument, instrument tip, and/or surgical tool continues at risk structures may be adversely affected.

The method 300 may include (at step 318), by at least one processor 705, generating a planned trajectory through which the interbody implant travels between the psoas and at least one vessel that is adjacent to and/or proximal to the vertebrae body for treatment. The planned trajectory may include identifying a change in an estimated pose of an implant at a location between the incision and the implant location associated with a selected vertebrae body, for example.

The machine-learning algorithms may employ feature extraction algorithms for detecting the objects (such as, the psoas, vessels, vertebrae body, and interbody implant) in captured images, for example. The feature extraction algorithms may include, without limitation, edge detection, corner detection, template matching, dynamic texture processing, segmentation image processing, object tracking, background subtraction, object recognition and classification, etc. When used in the context of autonomous surgery, the term "trajectory" may refer to the plan that the robot's motion planning system will generate, and which the robot's motion control system will follow when controlling the instrument's motion. A trajectory includes the instrument's planned position and orientation at multiple points in time over a time horizon, as well as, the planned position of the implant for example. During surgery, the location points of the trajectory may be consumed along a path, for example.

The method 300 may include (at step 320), by at least one processor 705, determining whether there is another vertebrae level, for example. If the determination (at step 320) is "NO," the method may end (at step 322, for example). If the determination (at 320) is "YES," the method 300 may include getting next level information (at step 324) of a next vertebra body to be treated, for example. The method 300 may loop to step 302 to start the process over again to find another trajectory to the next vertebrae body level to be treated thus beginning the above explained process once again, for example.

Figure 5:
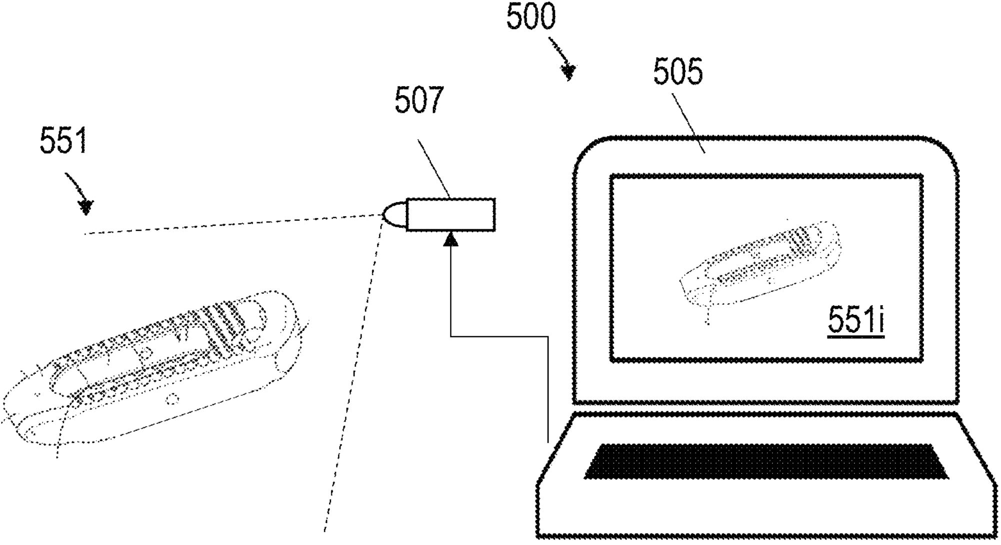
FIG. 5 is an example illustration of an interbody implant and image capture system to capture images of the interbody implant.

FIG. 5 is an example illustration of an interbody implant 551 and image capture system 500 to capture images 551*i* of the interbody implant 551, for example. The image capture system 500 may include a camera device or imaging device 507 configured to capture different perspective views of the interbody implant 551 to form different pose reference image(s), for example. In some embodiments, the geometry of the interbody implant 551 may have various configurations, such as, for example, cylindrical, round, oval, oblong, triangular, polygonal having planar or arcuate side portions, irregular, uniform, non-uniform, consistent, variable, horseshoe shape, U-shape or kidney-bean shape. In one embodiment, the interbody implant may include an agent. The agent may include therapeutic polynucleotides or polypeptides and bone growth promoting material, for example.

Figure 6:
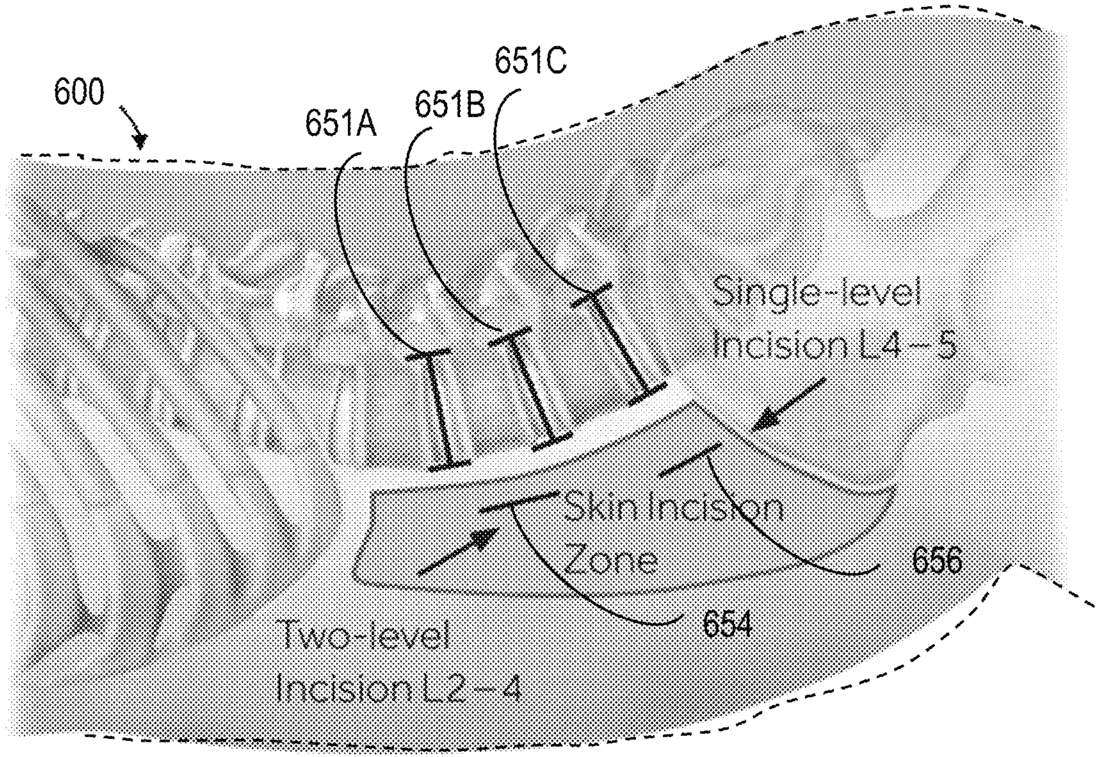
FIG. 6 is a perspective view that illustrates an example patient for planning an automatic OLIF corridor.

FIG. 6 is a perspective view that illustrates an example image 600 of a patient of which a planning procedure such as disclosed herein may include planning of an automatic OLIF corridor, for example. The image 600 may include simulated implants 651A, 651B, and 651C implanted between appropriate vertebra levels as part of the planning software, for example. In various embodiments, the simulated implants may refer to a digital representation of an actual physical implant to be installed in a patient, for example. The image 600 may include simulated incisions 654 and 656 from which the OLIF corridor may be planned to reach the vertebra, for example. In various embodiments, the simulated incisions 654 and 656 may represent an actual physical incision to be performed by a surgeon when installing the physical version of a respective implant, for example. In this illustration, two incisions are shown. However, there may be one or three or four incisions which may be separate incisions and/or coextensive incisions, for example.

FIG. 7 depicts an example systems diagram of various internal electronic hardware that may be included in any of the electronic components of an electronic device 700 as described in this disclosure such as, for example, a computing device, a remote server, cloud computing system, external electronic device and/or any other integrated system and/or hardware that may be used to contain or implement program instructions 722. Those with skill in the art will appreciate that such hardware need not be entirely embodied in any one form of hardware and rather can be distributed as needed amongst the various example computer systems disclosed above, for example.

A bus 710 may serve as the main information highway interconnecting the other illustrated components of the hardware, for example. Processor(s) 705 may be the central processing unit (CPU) of the computing system, performing machine-learning algorithms 723, calculations and/or logic operations as may be required to execute a program, for example. CPU 705, alone or in conjunction with one or more of the other elements disclosed in FIG. 7, may be an example of a processor as such term is used within this disclosure. Read only memory (ROM) and random access memory (RAM) constitute examples of various tangible and non-transitory computer-readable storage media, memory devices 720 or data stores as such terms are used within this disclosure. The memory device 720 may store an operating system (OS) of the computing device, a server or for the platform of the electronic device. The memory device 720 may store the machine-learning algorithms 723, such as for image segmentation 724, measurements for corridor planning 725 and predict path 726 based on the surgeon preferences. In various embodiments, memory device 720 may store images and computer executable code that performs the various methods and actions as disclosed herein.

Program instructions 722, software or interactive modules for providing the interface and performing any querying or analysis associated with one or more datasets 727 may be stored in the computer-readable storage media (e.g., memory device 720). Optionally, the program instructions 722 may be stored on a tangible, non-transitory computer-readable medium such as a compact disk, a digital disk, flash memory, a memory card, a universal serial bus (USB) drive, an optical disc storage medium and/or other recording medium, for example. The program instructions 722 may include instructions, which when executed by a processor and/or CPU generate a OLIF corridor planning tool 728. For example, such as for planning an OLIF corridor, as described in relation to FIGS. 2-3.

The memory device 720 may include a surgery navigation interface 775 to interface with the surgery navigation system 24 (see FIG. 1). An optional display interface 730 may permit information from the bus 710 to be displayed on the display device 732 in audio, visual, graphic or alphanumeric format, for example. Communication with external devices may occur using various communication ports 740. A communication port 740 may be attached to a communications network, such as the Internet or an intranet, for example. In various embodiments, communication with external devices may occur via one or more short range communication protocols such as Bluetooth, Zigbee, or a similar protocol. The communication port or devices 740 may include communication devices for wired or wireless communications and may communicate with a remote server 790 and/or a local server.

The hardware may also include a user interface 745, such as a graphical user interface (GUI), that allows for receipt of data from input devices, such as a keyboard or other input device 750 such as a mouse, a joystick, a touch screen, a remote control, a pointing device, a video input device and/or an audio input device, for example. The GUIs, described herein, may be displayed using a browser application being executed by an electronic device and/or served by a server (not shown). For example, hypertext markup language (HTML) may be used for designing the GUI 770 with HTML tags to the images of the patient and other information stored in or served from memory of the server (not shown). Another example may be an Application Programming Interface (API). The GUIs may be implemented using programming instructions, which when executed are configured to generate the GUI 770 and cause the display device 732 to selectively display the GUI.

In this document, "electronic communication" may refer to the transmission of data via one or more signals between two or more electronic devices, whether through a wired or wireless network, and whether directly or indirectly via one or more intermediary devices. Devices are "communicatively connected" and/or "in communication" if the devices are able to send and/or receive data via electronic communication, for example.

In one or more examples, the described techniques and methods may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that may be used to store desired program code in the form of instructions or data structures and that may be accessed by a computer).

Instructions 722 may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

As used herein, the term "about" in reference to a numerical value means plus or minus 10% of the numerical value of the number with which it is being used. The features and functions described above, as well as alternatives, may be combined into many other different systems or applications. Various alternatives, modifications, variations or improvements may be made by those skilled in the art, each of which is also intended to be encompassed by the disclosed embodiments.

What is claimed is:

1. A surgical navigation and planning system, comprising:

a display device;

at least one processor; and a non-transitory and tangible computer readable storage medium having programming instructions stored thereon, which when executed by the at least one processor cause the at least one processor to:

receive patient-specific vertebrae information associated with a vertebrae level for treatment of a patient, the patient-specific vertebrae information comprising at least one image;

identify a plurality of objects in the at least one image, the plurality of objects including a psoas muscle and vessels proximate to the psoas muscle;

based on the identified plurality of objects, automatically determine a first path and orientation for an interbody implant from a first simulated incision location to a location proximal the vertebrae level;

calculate, based on the first path, a first plurality of clearance distances between boundary dimensions of the interbody implant and the identified objects; and responsive to the first path navigating around the identified objects by at least a margin of error, cause the display device to display a surgical plan including the first path.

2. The surgical navigation and planning system of claim 1, wherein the programming instructions further cause the at least one processor to:

determine a plurality of paths for the interbody implant from the first simulated incision location to the location proximal the vertebrae level;

for each of the plurality of paths, calculate clearance distances between the boundary dimensions of the interbody implant and the identified objects; and rank the plurality of paths based on the calculated clearance distances.

3. The surgical navigation and planning system of claim 1, wherein the programming instructions that cause the at least one processor to identify the plurality of objects in the at least one image comprise programming instructions that cause the at least one processor to apply a trained neural network to the at least one image.

4. The surgical navigation and planning system of claim 1, wherein the programming instructions that cause the at least one processor to cause the display device to display the surgical plan comprise programming instructions that cause the at least one processor to cause the display device to display the identified objects and the calculated clearance distances.

5. The surgical navigation and planning system of claim 1, wherein the margin of error is a programmable margin of error.

6. The surgical navigation and planning system of claim 1, wherein the programming instructions that cause the at least one processor to identify the vessels proximate to the psoas muscle comprise programming instructions that cause the processor to identify an Aorta and/or a Vena Cava.

7. The surgical navigation and planning system of claim 1, wherein the computer readable storage medium further comprises one or more programming instructions that, when executed by the at least one processor cause the at least one processor to:

determine a second simulated incision location;

determine a second path for the interbody implant from the second simulated incision location to the location proximal the vertebrae level; and calculate, based on the second path, a second plurality of clearance distances between the boundary dimensions of the interbody implant and the identified objects.

8. The surgical navigation and planning system of claim 7, wherein the computer readable storage medium further comprises programming instructions that, when executed by the at least one processor cause the at least one processor to:

perform a comparison of the first plurality of clearance distances to the second plurality of clearance distances; and rank the first path and the second path based on the comparison of the first plurality of clearance distances and the second plurality of clearance distances.

9. The surgical navigation and planning system of claim 8, wherein the computer readable storage medium further comprises programming instructions that, when executed by the at least one processor cause the at least one processor to cause the display device to display the ranking of the first path and the second path.

10. The surgical navigation and planning system of claim 9, wherein the computer readable storage medium further comprises programming instructions that, when executed by the at least one processor cause the at least one processor to cause the display device to display the comparison of the first plurality of clearance distances and the second plurality of clearance distances in a customizable graphical user interface.

11. The surgical navigation and planning system of claim 1, wherein the computer readable storage medium further comprises one or more programming instructions that, when executed by the at least one processor cause the at least one processor to receive aggregated historical data comprising clinical outcomes of completed surgeries utilizing a substantially similar interbody device.

12. The surgical navigation and planning system of claim 1, wherein the computer readable storage medium further comprises one or more programming instructions that, when executed by the at least one processor cause the at least one processor to receive individual surgeon preferences.

13. The surgical navigation and planning system of claim 1, further comprising an imaging system including a source for generating X-rays and a detector for detecting X-rays that pass through the patient.

14. The surgical navigation and planning system of claim 13, wherein the computer readable storage medium further comprises one or more programming instructions that, when executed by the at least one processor cause the at least one processor to receive the patient-specific vertebrae information comprising the at least one image from the imaging system.

15. The surgical navigation and planning system of claim 1, further comprising a navigation system configured to register the first path with the patient.

16. The surgical navigation and planning system of claim 15, wherein the navigation system is further configured to track an instrument relative to the patient.

17. A method for determining a corridor for inserting an interbody implant, comprising:

receiving patient-specific vertebrae information associated with a vertebrae level for treatment of a patient, patient-specific vertebrae information comprising at least one image;

identifying a plurality of objects in the at least one image, the plurality of objects including a psoas muscle and vessels proximate to the psoas muscle;

based on the identified plurality of objects, determining a first path and orientation for an interbody implant from a first simulated incision location to a location proximal the vertebrae level;

calculating, based on the first path, a first plurality of clearance distances between boundary dimensions of the interbody implant and the identified objects; and responsive to the first path navigating around the identified objects by at least a margin of error, causing a display device to display a surgical plan including the first path.

18. The method of claim 17, further comprising registering a navigation system with the patient.

19. The method of claim 18, further comprising tracking a position of the interbody implant along the corridor during the treatment of the patient.

20. The method of claim 19, further comprising displaying the tracked position of the interbody implant.

* * * * *